US005338666A

United States Patent [19]

Monthony et al.

[11] Patent Number: 5,338,666

[45] Date of Patent: Aug. 16, 1994

[54] METHOD FOR DISTRIBUTING A LIQUID SAMPLE INTO A MULTIPLE ALIQUOT DEVICE

[75] Inventors: James F. Monthony, Baltimore; Dwight Livingston, Towson; Jayakumar Reuben, Fallston; Robert C. Tite, Baltimore, all of Md.

[73] Assignee: Becton, Dickinson and Company, Franklin Lakes, N.J.

[21] Appl. No.: 860,841

[22] Filed: Mar. 31, 1992

Related U.S. Application Data

[62] Division of Ser. No. 644,786, Jan. 23, 1991, Pat. No. 5,182,082.

[51] Int. Cl.[5] .......................... C12Q 1/04; C12Q 1/24

[52] U.S. Cl. ........................................ 435/34; 422/57; 422/58; 422/99; 435/30; 435/293

[58] Field of Search ............ 435/30, 34, 287, 292–294; 422/99–100, 102–104, 50, 61, 55, 58, 57

[56] References Cited

U.S. PATENT DOCUMENTS

| | | | |
|---|---|---|---|
| Re. 29,955 | 4/1979 | Bornstein et al. . | |
| 3,826,717 | 7/1974 | Gilbert et al. . | |
| 3,957,583 | 5/1976 | Gibson et al. . | |
| 4,018,652 | 4/1977 | Lanham et al. . | |
| 4,076,592 | 2/1978 | Bradley . | |
| 4,116,775 | 9/1978 | Charles et al. . | |
| 4,154,795 | 5/1979 | Thorne . | |
| 4,200,613 | 4/1980 | Alfrey et al. . | |
| 4,207,394 | 6/1980 | Aldridge, Jr. et al. . | |
| 4,235,971 | 11/1980 | Howard et al. . | |
| 4,239,853 | 12/1980 | Bradley . | |
| 4,294,024 | 10/1981 | Pepicelli et al. | 435/30 |
| 4,342,407 | 8/1982 | Citrin . | |
| 4,483,925 | 11/1984 | Noack . | |
| 4,493,896 | 1/1985 | La Motte, III et al. . | |
| 4,496,657 | 1/1985 | Coppersmith et al. . | |
| 4,532,805 | 8/1985 | Flesher . | |
| 4,548,245 | 10/1985 | Crandell et al. . | |
| 4,565,100 | 1/1986 | Malinoff . | |
| 4,761,378 | 8/1988 | Godsey . | |
| 4,806,316 | 2/1989 | Johnson et al. . | |

OTHER PUBLICATIONS

Brochure for F.A.S.T.TM Immunoassay System (trademark of Becton, Dickinson and Company) by Becton Dickinson Labware Products, Lincoln Park, N.J.

*Primary Examiner*—Robert J. Warden
*Assistant Examiner*—Krisanne M. Thornton
*Attorney, Agent, or Firm*—Nanette S. Thomas

[57] ABSTRACT

A method for receiving, distributing and storing a sample into numerous aliquots of small volume without air entrapment and with retention of aliquots when the device is manipulated and for the treatment of any or all of the aliquots with the same or different reagents and/or other chemical additives.

2 Claims, 12 Drawing Sheets

METHOD FOR DISTRIBUTING A LIQUID SAMPLE INTO A MULTIPLE ALIQUOT DEVICE

This is a divisional of co-pending application Ser. No. 07/644,786 filed Jan. 23, 1991 now U.S. Pat. No. 5,182,082.

BACKGROUND OF THE INVENTION

1. Field of the Invention

This invention relates to a device useful for receiving, distributing and storing aliquots of a sample for testing or analysis and is particularly useful in the sampling techniques employed in clinical microbiology applications.

2. Description of Related Art

There are many analytical methods in chemistry, clinical chemistry and microbiology where a liquid sample is divided into more than one aliquot and then tested or examined. Even in the case of a single analytical protocol, there are many instances where replicate tests may be run on multiple aliquots of the sample to assure reproducibility of the result. When undergoing analysis and characterization, aliquots of a single sample may be reacted with either a variety of different chemical reagents for analytical purposes or may be reacted with differing amounts of a single reagent or both.

Many approaches exist to aid in the preparation of aliquots of a single sample. A common example of such a situation exists in the modern practice of clinical microbiology. An unidentified microorganism is routinely subjected to tests and procedures to determine its identity and/or pattern of resistance or susceptibility to destruction by a variety of antimicrobic chemicals. Commercial systems for such determination are provided by several manufacturers and typically use between 10 and 100 small aliquots of a sample suspension of the microorganism undergoing analysis. These systems require a variety of sterile vessels and pipetting aids for adequate filling when small physical amounts of aliquots are required. Therefore a need exists for a device and method for the preparation of sample aliquots that obviates the requirement for a variety of sterile vessels and pipetting aids.

A number of devices and containers are commercially available for the preparation of samples for analysis. For in vitro tests, disposable, multi-compartmental containers are provided by manufacturers in complete reagent kits. Immunoassays, which include the screening of blood samples for virus antibodies (e.g., the HIV or Hepatitis B virus), are commonly carried out in 96 well micro titration trays supplied precoated with appropriate reagents as part of a kit. Specialized equipment used in the preparation of samples for analysis is described in U.S. Pat. Nos. 4,761,378; 4,496,657; 4,493,896; 4,342,407; 3,826,717; 4,154,795 and 4,200,613.

Pipetting devices for inoculation of multi-compartmental containers include the SCEPTORPETTE® System (trademark of Becton Dickinson and Company) sold by Becton Dickinson Microbiology Systems, Towson, Md. and the device illustrated in U.S. Pat. No. 4,532,805.

In clinical microbiology, there are a number of devices and containers available, having a plurality of small reaction chambers. Such devices include the SCEPTOR® Bacterial MIC and ID testing system (trademark of Becton Dickinson and Company) sold by Becton Dickinson Diagnostic Instrument Systems, Towson, Md., MINITEK™ Systems (trademark of Becton Dickinson and Company) sold by Becton Dickinson Microbiology Systems, Cockeysville, Md. and the API20E® Identification Strip (trademark of Sherwood Medical) sold by Analytab Products, Division of Sherwood Medical, Plainview, N.Y.

Devices for manipulating liquid samples containing microorganisms for use with multi-welled containers are described in U.S. Pat. Nos. 4,548,245; 4,565,100; 4,239,853; 4,235,971; and 4,076,592.

Automated devices for microorganism identification and drug susceptibility testing include the commercially available VITEK™ system (trademark of Vitek Systems, Inc.) sold by Vitek Systems, Inc., Hazelwood, Mo. and the devices illustrated in U.S. Pat. Nos. 3,957,583; 4,018,652; 4,116,775 and 4,207,394.

U.S. Pat. No. 4,806,316 to Johnson, et. al. describes a device for use in exposing a sample to be tested to one or more test reactants. The Johnson et al. device comprises a docking port, a filling manifold, a vent control system and a filling channel. A specific feature of the device is that it uses complex flow paths for liquid and air.

A device comprising a planar surface with projections which align with the wells of a standard-type 96 well tissue culture plate is known in the art as shown in U.S. Pat. No. 4,483,925 to Noack. The projections used in Noack are of an absorbent nature and are used to control the removal of liquid from the wells.

A commercially available system, the F.A.S.T.™ Immunoassay System (trademark of Becton Dickinson and Company) by Becton Dickinson Labware Products, Lincoln Park, N.J., provides simultaneous addition of a reagent to wells of a microtiter plate, however, each well of the microtiter plate is previously filled by pipetting steps.

Although there are a number of testing devices and pipetting systems available, there is no self-contained system available to produce small aliquots of a sample without entrapment of air bubbles.

The available devices also do not allow easy error-free reading of reaction results visually or by instruments for accurate test results, particularly when covered. The available devices do not have the means to provide aliquots of predetermined volume in a single operation and are not able to conveniently or accurately introduce reagents or materials into each separate aliquot for analysis thereof.

Thus, a special need exists for a device and method for the convenient preparation of separate aliquots into efficient areas without entrapment of air that obviates the requirement for a variety of sterile vessels, pipetting aids and multiple manipulations.

SUMMARY OF THE INVENTION

The present invention is a device for dividing and air filling sample into efficient aliquots without entrapment and with retention of the aliquots. The device comprises a housing and a body for guiding sample into a plurality of wells and for retaining the sample in the wells for testing and analysis.

In a preferred embodiment of the invention, the device comprises an outer-base element and a sample distribution element for dividing a sample into pre-determined volume aliquots.

The outer-base element preferably comprises a bottom, an inner planar surface, depending side walls and individual well bottoms raised from the inner planar surface.

The outer-base element preferably comprises a plurality of posts projecting from its inner planar surface and the sample distribution element may have a plurality of corresponding bosses depending from its lower surface. The bosses engage the posts thereby securing the outer-base element to the sample distribution element so as to form a device.

The sample distribution element provides for receiving, distributing, filling and holding sample material and comprises an upper surface, a lower surface, and a plurality of wells. The sample distribution element is associated with the outer-base element and the outer-base element preferably serves as the base to the sample distribution element.

A preferred embodiment of the sample distribution element comprises a means for containing and/or guiding the sample sequentially over the upper surface of the sample distribution element. This means is a trough which comprises a unidirectional pathway on the upper surface of the sample distribution element.

Another preferred embodiment of the sample distribution element comprises a means for receiving and/or distributing sample and/or for holding excess sample. This means is a reservoir area adjacent to the trough.

Each well is substantially disposed between the upper and lower surface of the sample distribution element and transversely disposed with respect to the trough. Each well comprises a sidewall, a sidewall bottom surface, an upper mouth opening and a bottom mouth opening. The bottom mouth opening and the sidewall bottom surface of each well corresponds with the well bottoms raised from the inner planar surface of the outer-base element.

Preferably, the upper mouth opening and the trough are substantially perpendicular to each other to form a substantially sharp junction. It is believed that the substantially sharp junction provides a means for separating individual aliquots from the sample.

Preferably, the bottom mouth opening and the sidewall bottom surface are substantially parallel to the well bottom to form a sufficiently spaced means between them so that air is expelled from the well and the aliquot easily fills into the well. It is believed that the weight of the sample forces the air in the well to be pushed through the spaced means. It is further believed that the combination of frictional forces, hydrostatic pressure differential and the sample surface tension prevents the aliquot from leaving the well or spaced means even when the device is manipulated or inverted. It is also believed that the spaced means allows the diameter of the individual wells to be of a substantially small size and to also allow the aliquot to easily fill into individual small wells without any restriction and without the need for pipetting aids.

The device preferably comprises a removable lid associated within the outer-base element and over the sample distribution element, which includes an upper and lower .surface, depending sidewalls and a plurality of projections depending from its lower surface. The lid serves to prevent the loss of sample or aliquots from the device interior, to protect the contents of the device from the environment, to protect the user from the contents of the device should it contain a harmful or potentially harmful material such as a microorganism suspension and to provide a means for testing aliquots.

A majority of the projections on the lid are preferably arrayed, sized and shaped to fit within the upper mouth opening of each well in the sample distribution element.

Projections depending from the lid preferably are coated with materials to interact with the sample aliquot in the individual wells. Alternatively, one or more conduits may be on the upper surface of the lid and connected to one or more of the projections. Materials may be added to wells via the conduits after the lid has been placed over the sample distribution element. Materials added to the wells by the conduit and the projections may be in addition to materials coated on the projections.

A preferred embodiment of the lid comprises means for absorbing excess sample in the reservoir of the sample distribution element which means is preferably a sponge or absorbent pad.

The preferable form of the device is a rectangular shape with the wells in an ordered array of parallel rows. The outer-base element and the lid are preferably made of an optically clear plastic to facilitate viewing of the wells. The sample distribution element is preferably made of an opaque color, most preferably white, so as to provide contrast and prevent interference of colored sample in the wells with one another.

The device preferably receives, divides and distributes a sample into individual wells that are of a substantially small volume comprising a small diameter and/or height for testing and/or analysis. A sample is provided in the reservoir of the sample distribution element and the wells are filled by tilting the device slightly so that the sample in the reservoir flows in the unidirectional pathway of the trough. Once the sample has traveled to the last well, the device can be tilted to make any excess sample travel back along the same pathway to the reservoir. This process assures that sample passes over the upper mouth of each well twice to ensure complete filling. As the sample flows from the opening of each well downward, air is expelled from the well through the spaced means between the sidewall bottom surface of the well and the well bottom. The substantially sharp junction of the upper mouth opening of each well and the trough provides a means for separating individual aliquots from the sample into the well.

Sample may enter the spaced means between the sidewall bottom surface of the well and the well bottom after air has been expelled, and it is believed that the combination of frictional forces, hydrostatic pressure differential and the sample surface tension prevents the sample from flowing beyond the spaced means between the sidewall bottom surface of the well and the well bottom. As excess sample continues in the trough, the aliquot is -separated from the - sample by the substantially-sharp junction of the upper mouth opening of each well and the trough. The sample easily fills into each well and pushes air through the spaced means. The sample remains in the well and in the spaced means even when the device is manipulated or inverted.

The spaced means allows the aliquot to fill into individual wells of a small volume comprising a small diameter and/or height without any restriction.

The individual wells may be coated with dried reagents that are reconstituted with fluid from the sample or with immobilized reagents for solid phase tests. More preferably, additional wet or dry reagents may be coated on the projections depending from the lid. Upon covering of the device with the lid these additional reagents come into contact with the sample in the wells.

In accordance with the preferred embodiment of the present invention, the device is chemically isolated, and well-suited for use in clinical microbiology applications including, but not limited to, chemical, immunochemical and microorganism identification and antimicrobic sensitivity testing.

The device is disposable, self-contained and is able to produce aliquots of substantially small volume in a rapid manner without a variety of sterile vessels, pipetting or sampling aids and multiple manipulations.

The device solves the problem of filling an aliquot into a small volume comprising a small diameter and/or height, without the need for pipetting or sampling aids and multiple manipulations.

An advantage of the device is that it is able to allow isolation of sample aliquots so they may be reacted or modified in an individually selective manner. The multiple aliquots may be treated with the same or different reagents or other chemical additives.

A further advantage is that the device provides a convenient means for simultaneously and effectively inoculating a large number of individual wells of a small volume comprising a small diameter and/or height, without the need for multiple filling and distributing steps.

Another advantage of the device is that air is easily expelled from each well so that the sample may easily fill into each well and also so that the aliquot remains in the well even upon manipulating or inverting the device.

A further advantage of the device is that consistent results may be obtained when testing the sample because of the substantially equal, rapid and reproducible filling of each well, the substantially equal volume of all the aliquots and because air has been expelled from the wells during filling.

The device also allows for easy visual or machine examination of individual sample aliquots and reduces the total amount of starting sample required for use by allowing aliquots of a small volume to be distributed.

With the foregoing and additional features in view, this invention will now be described in more detail, and other benefits and advantages thereof will be apparent from the following description, the accompanying drawings, and the appended claims.

BRIEF DESCRIPTION OF THE DRAWINGS

A further understanding of the invention may be achieved by referring to the accompanying drawings, wherein:

FIG. 2(*a*) is a top view of the outer-base element of FIG. 2.

FIG. 3(*a*) is a top view of the sample distribution element of FIG.

FIG. 3(*b*) is a bottom view of the sample distribution element of FIG 3.

FIG. 4(*a*) is an enlarged partial cross-sectional perspective view of the assembled components of the embodiment of FIG. 1, illustrating the well, the well bottom and the projections on the periphery of the well bottom.

FIG. 4(*b*) is an enlarged partial cross-sectional perspective view of the assembled components of FIG. 1, illustrating the well, the sidewall bottom surface and the projections on the periphery of the sidewall bottom surface.

DETAILED DESCRIPTION

Figure 1:
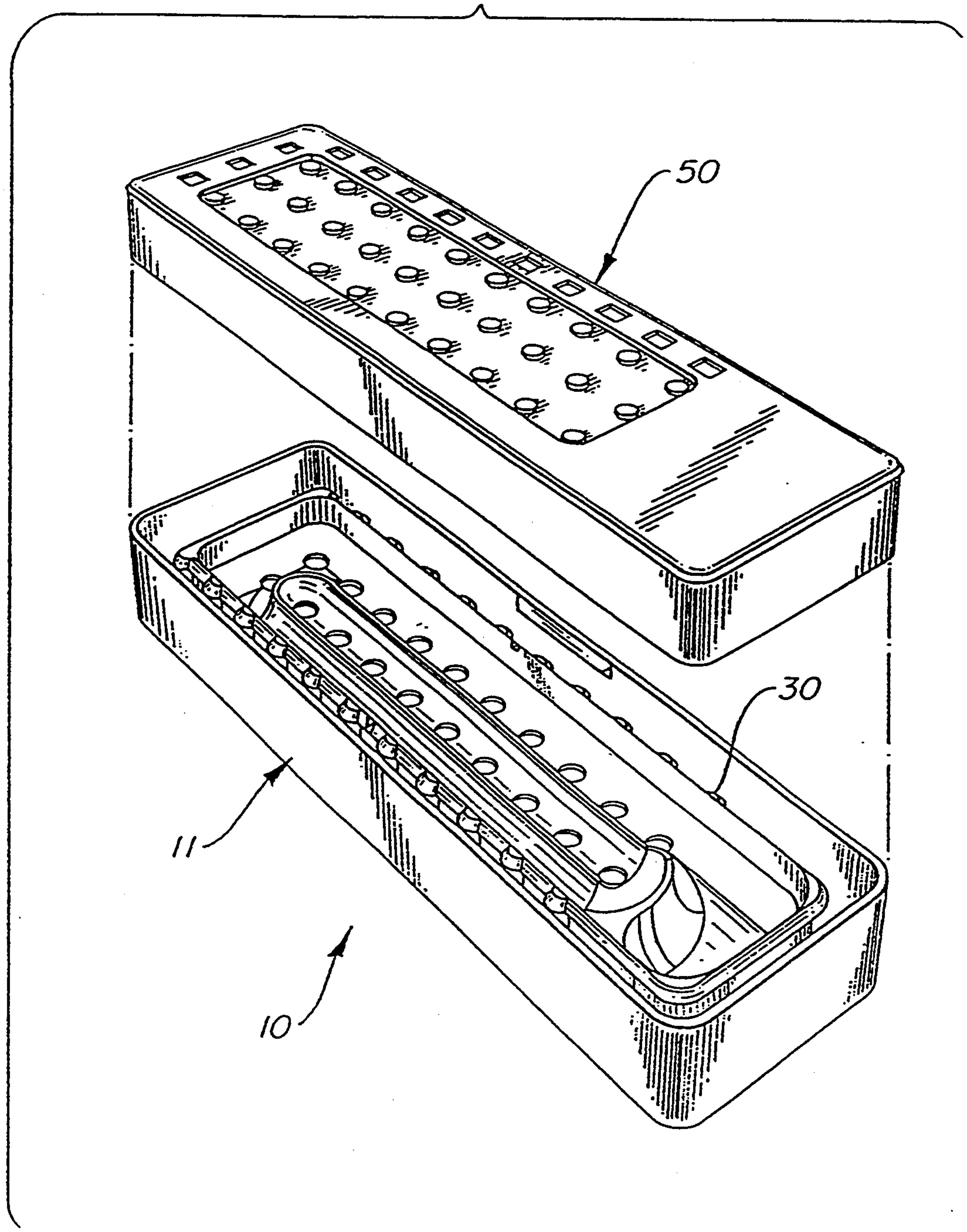
FIG. 1 is a perspective view of the preferred embodiment of the invention illustrating the outer-base element connected to the sample distribution element with the optional removable lid not attached.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from .the scope and spirit of the invention. The scope of the invention will be measured by the appended claims and their equivalents.

Referring to the drawings, there is illustrated a device according to the present invention for receiving, distributing and storing multiple aliquots of a sample to be tested or analyzed.

The preferred embodiment of device 10 comprises an outer-base element 11, a sample distribution element 30 and a lid 50 as shown in FIG. 1.

Device 10 is typically, but not limited to, a rectangular shape with the wells in an ordered array of parallel rows. The outer-base element and the lid are preferably an optically clear plastic to facilitate viewing of the wells. The sample distribution element is preferably made of an opaque colored plastic, most preferably white plastic, to provide contrast and prevent interference of colored sample in the wells with one another.

Figure 2:
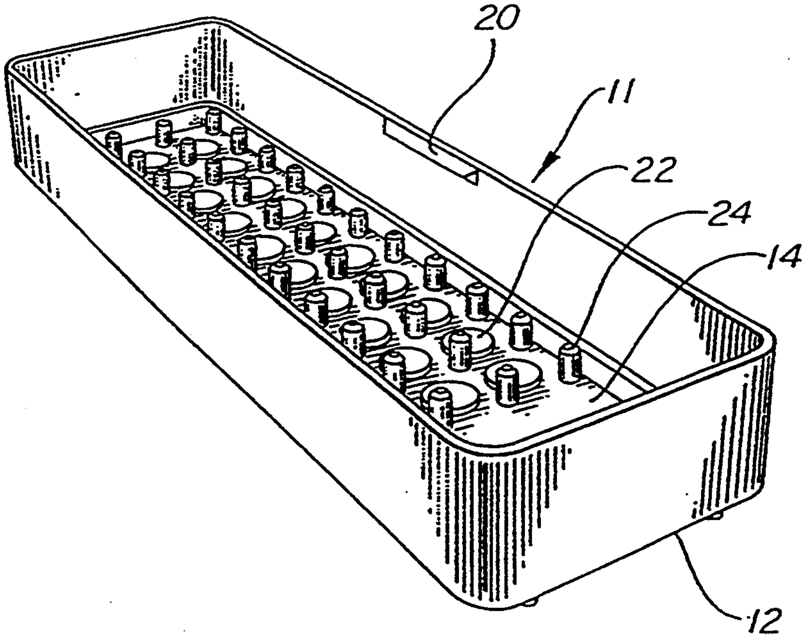
FIG. 2 is a perspective view illustrating the outer-base element.
Figure 2A:
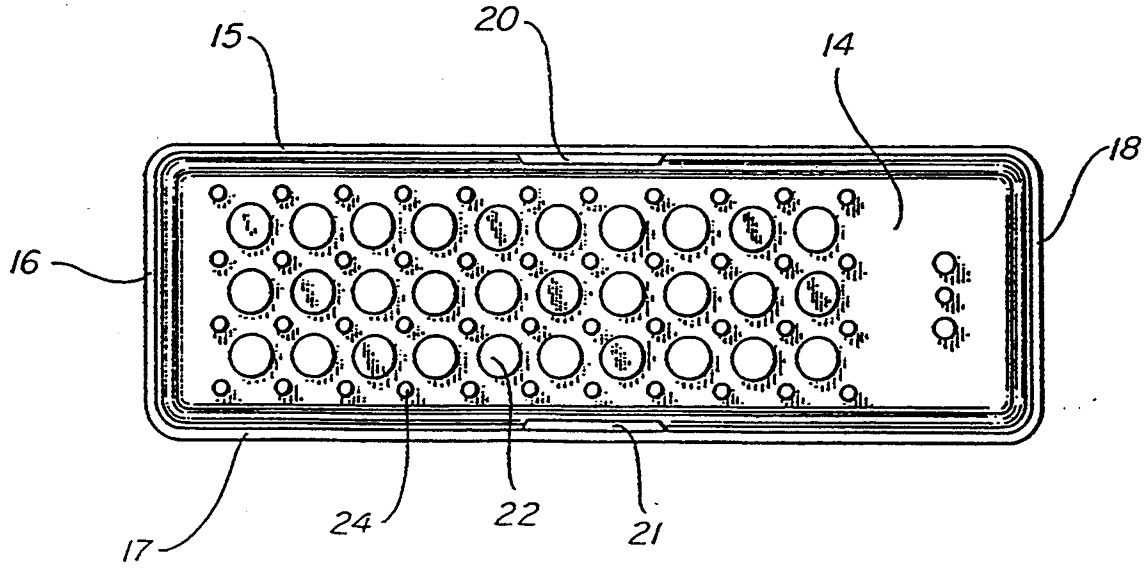

The outer-base element 11 as shown in FIGS. 2 and 2(*a*) comprises a bottom 12, an inner planar surface 14, depending sidewalls 15, 16, 17 and 18, shelf-like projections 20 and 21 located on the inner side of two opposite sidewalls, circular well bottoms 22 slightly raised from inner planar surface 14 and attachment posts 24 raised from the inner planar surface. Sidewalls 15, 16, 17 and 18 meet and are substantially perpendicular with inner planar surface 14.

Figure 3:
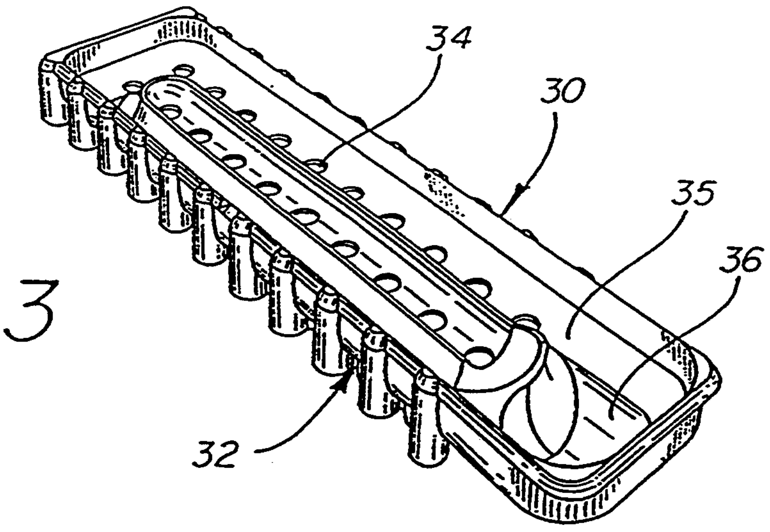
FIG. 3 is a perspective view illustrating the sample distribution element.
Figure 3A:
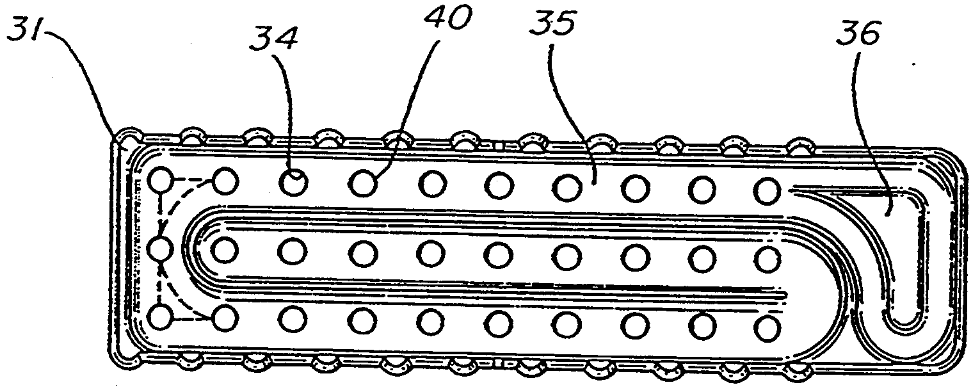
Figure 3B:
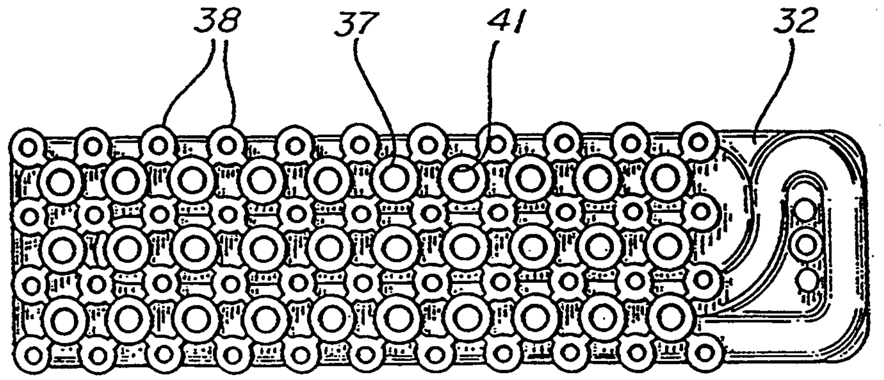

Sample distribution element 30 as shown in FIGS. 3, 3(*a*) and 3(*b*) comprises an upper surface 31, a lower surface 32, wells 34, a trough 35, a reservoir 36 and attachment bosses 38. The sample distribution element is preferably disposed within the outer-base element.

Each well 34 in sample distribution element 30 is substantially disposed between upper surface 31 and lower surface 32 and transversely disposed with respect to trough 35. Each well comprises a circular sidewall 39, a sidewall bottom surface 37, an upper mouth opening 40 and a bottom mouth opening Each well is substantially perpendicular to the trough to form a substantially sharp junction at the upper mouth opening. It is believed that the substantially sharp junction provides a means for effectively and efficiently separating individual aliquots from the sample.

Each well size may be varied by changing well cross-section or depth. The wells are shown in a circular configuration, but may have any cross-sectional geometry. The wells preferably are in a three by ten matrix of thirty equal sizes as shown in FIG. 3(*a*). The bottom mouth opening of each well corresponds with a well bottom of the outer-base element as shown in FIG. 4.

Figure 4:
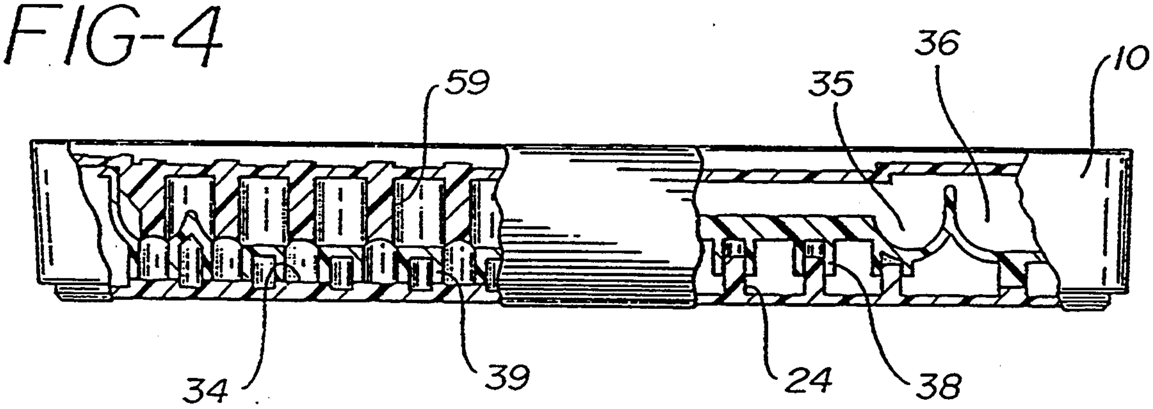
FIG. 4 is a partial cross-sectional side elevational view, illustrating the assembled components of the embodiment of FIG. 1.
Figure 4A:
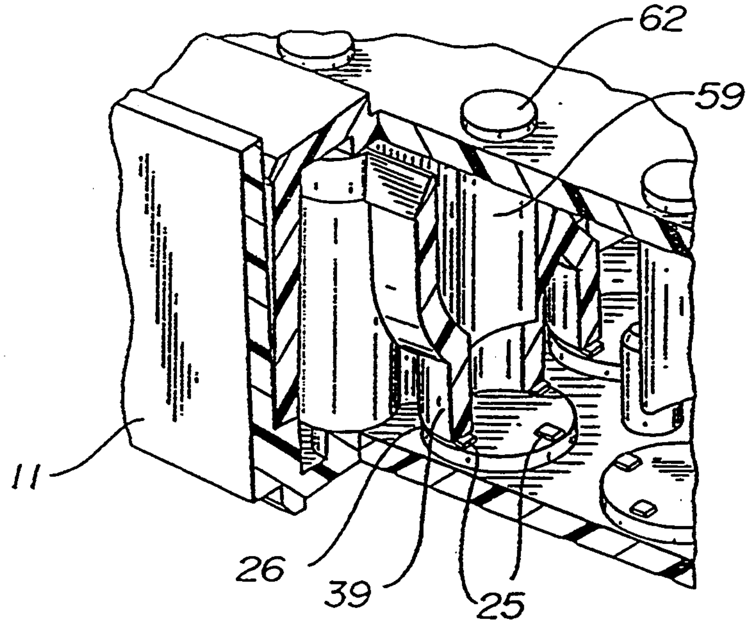
Figure 4B:
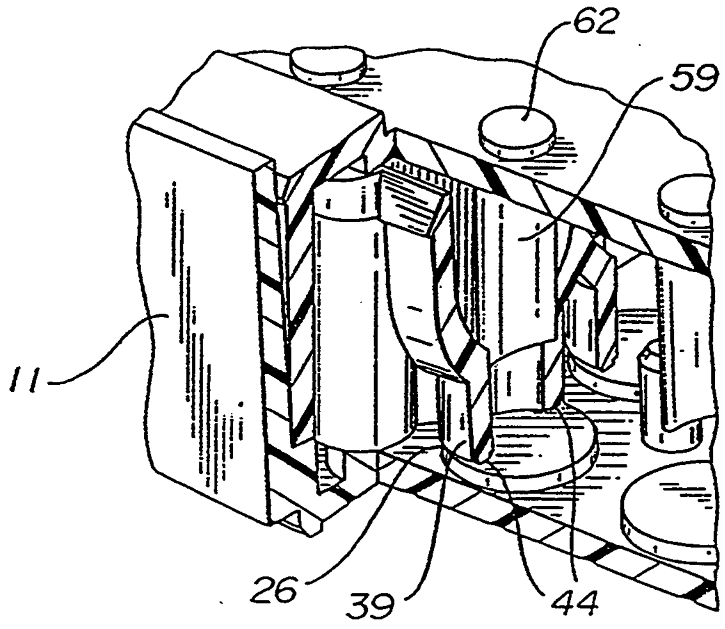

Attachment posts 24 of the outer-base element mate with corresponding attachment bosses 38 on the sample distribution element to secure the sample distribution element to the outer-base element as also shown in FIG. 4.

Preferably the device is formed wherein sidewall bottom surface 37 and circular well bottom 22 are not sealed or-fastened to each other. As shown in FIG. 4 the sidewall bottom surface and the well bottom are preferably substantially parallel to each other to form a variable space 26 between them for allowing only air to escape from the wells as sample enters.

Projections 25 may be on the periphery surface of well bottoms 22 as shown in FIG. 4(*a*) or as projections 44 on the periphery surface of the sidewall bottom surface 37 as shown in FIG. 4(*b*) so as to vary the space between the sidewall bottom surface and the well bottom. Most preferably, on the periphery surface of the well bottom or the sidewall bottom surface is a textured or abraded surface formed by abrasion, texturing, sanding or the like.

Sample distribution element 30 preferably comprises a reservoir 36 for receiving, distributing and/or storing liquid sample and/or for holding excess sample, which is connected to trough 35. Sample is poured or pipetted into the reservoir and then enters the trough. Preferably, the trough is a unidirectional pathway substantially perpendicular to the mouth opening of all the wells, ending at the last well and beginning at the reservoir.

Sample is distributed to each well by the trough by manually tilting the device slightly so that the sample in the reservoir flows in the trough. Once the sample has traveled to the last well, and if there is excess sample, the device is again tilted to make any undistributed sample pass back along the same path to the reservoir. The trough assures that a sample is allowed to pass over each well two times for complete filling. The sharp junction of the upper mouth opening and the trough provides a means for effectively and efficiently separating individual aliquots from the sample.

The sample flows from the upper mouth opening of each well through to the variable space between the sidewall bottom surface of the well and the well bottom after air has been expelled. It is believed that the weight of the sample forces the air or air bubbles to be pushed through the variable space. It is further believed that the combination of frictional forces, hydrostatic pressure differential and the sample surface tension prevents the sample from flowing beyond the variable space between the sidewall bottom surface of the well and the well bottom. Furthermore, the sample remains in the well and in the variable space between the sidewall bottom surface of the well and the well bottom even when the device is manipulated or inverted. The removal and prevention of air in each well allows for accurate, consistent and efficient testing and analysis of each aliquot.

The filling features of the present invention provide a means for distributing a small volume of an aliquot. The filling features are most useful when the upper mouth opening of each individual well is of a small diameter and/or the well circular sidewall is a small height. The small diameter of the upper mouth opening is allowed because of the function of the spaced means.

The upper mouth opening of each well is preferably from about 0.01 inches (0.03 cm) in diameter to about 0.25 inches (0.64 cm) and most preferably at about 0.16 inches (0.41 cm). Each well circular sidewall is preferably less than about 2 inches (5 cm) in height, desirably from about 0.04 inches (0.1 cm) to about 2 inches (5 cm) and most preferably at about 0.16 inches (0.41 cm).

The individual wells may also be coated with dried reagents that are reconstituted by the liquid sample or with immobilized reagents for solid phase tests.

Figure 5:
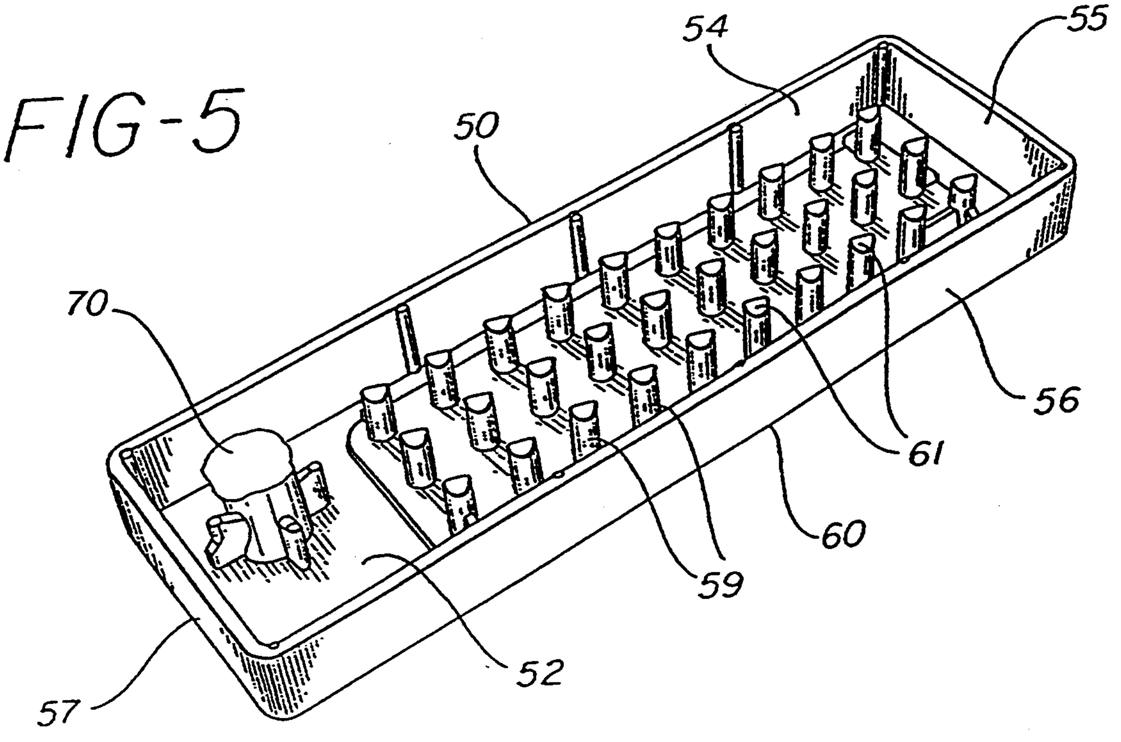
FIG. 5 is a perspective view of the removable lid of FIG. 1 with a means for absorption of sample.

As shown in FIG. 5, removable lid 50 comprises an upper surface 51, a lower surface 52, a depending edge 60 and depending sidewalls 54, 55, 56 and 57. The removable lid also further comprises a plurality of projections 59 raised from lower surface 52 with a tip 61 on the unconnected end of each projection. Sidewalls 54, 55, 56 and 57 meet and are substantially perpendicular with lower surface 52. Depending edge 60 is substantially perpendicular to the sidewalls and follows the perimeter of upper surface 51.

The lid removably covers the sample distribution element disposed within the outer base element. Sidewalls 54, 55, 56 and 57 and depending edge 60 serve to mate closely with outer-base element 11 forming a humidity control system for restricting evaporation of liquid from the device. Most preferably used to hold the lid and the outer-base element together are shelf-like projections 20 and 21 on the outer-base element and depending edge 60 on the lid.

Figure 5A:
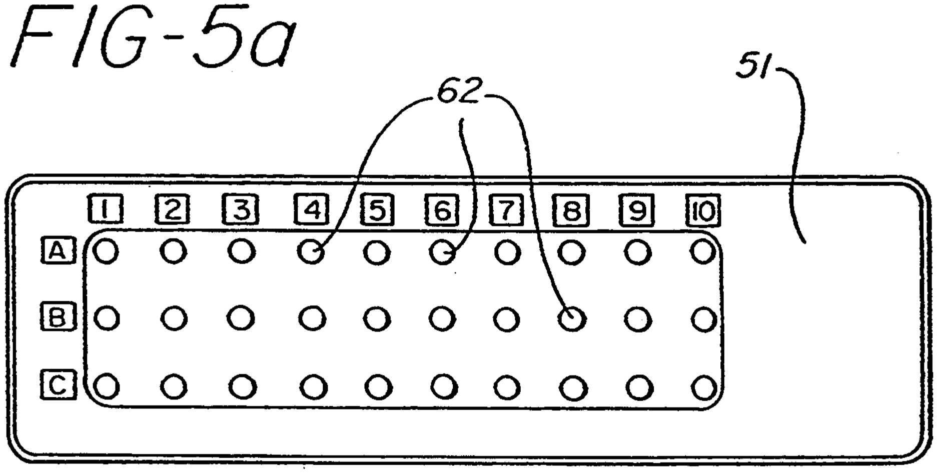
FIG. 5*a* is a top view of the removable lid of FIG. 1.

As is shown in FIG. 5*a*, various labels and identifying marks are preferably applied or molded into the lid of the device.

A most preferred embodiment of lid 50 is wherein a sponge or absorbent pad 70 is on the lower surface of the lid to draw up any excess sample from reservoir 36 of the sample distribution element as illustrated in FIG. 5.

Each projection on the lid is preferably arranged to align with each well. As shown in FIG. 4, each projection is slightly smaller in dimension than each well upper mouth opening and is preferably of a length such that it just touches the surface of the liquid aliquot in each well after filling.

Tip 61 on each projection is preferably precoated with reagents for delivery to the aliquot in each well.

Each projection, preferably has a one-to-one correspondence with each well, to provide a means for each well to be separately and individually reacted with chemical reagents or other materials for typical analytical purposes.

The lid optionally has circular optical extensions 62 which are raised up from upper surface 51 of the lid and connected to a projection as shown in FIG. 5. Extensions 62 may be used to view an optical path for visual or machine examination of the sample through projections 59 and through the aliquot in the well to well bottom 22.

The extensions and the projections serve to enhance the optical path of the device and eliminate problems from condensation common with simple lids due to their contact with the aliquot in each well. These components eliminate liquid to air and air to plastic interfaces in the viewing path of the well and the lid.

Figure 6:
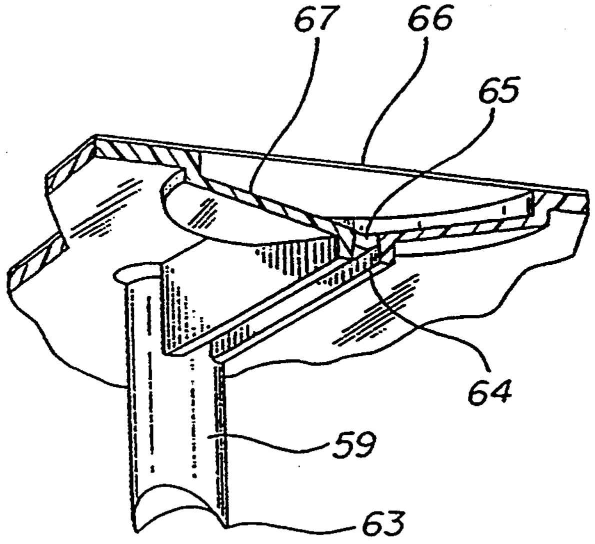
FIG. 6 illustrates an optional embodiment of the removable lid comprising conduits.

The lid optionally has a sealable opening 65 for adding liquid reagents to the aliquots in the wells. As shown in FIG. 6, the sealable opening is on the upper surface of the lid and may be effectively covered by sealing tape 66 affixed to the lid over opening 65. The sealable opening is surrounded by a funnel area 67 for easy access of reagent to be added to the opening. The tape can be removed by use of a tape pull tab which is not sealed to the lid. Liquid sample is dispensed into the opening and flows through the funnel and then to a conduit 64 which is molded into the lower surface of the lid and connected to the opening. Each conduit is preferably rectangular in cross section and directs flow of the sample to projection 59. In this embodiment, the projection further comprises a concave surface 63 for receiving liquid reagents for delivery or drying. Sealable opening 65 and conduit 64 may be connected to more than one projection to add a single reagent to multiple sample aliquots in their individual wells.

Additionally, lid 50 serves to protect the user from the contents of the device should it contain a harmful or potentially harmful material such as a microorganism suspension. In the preferred embodiment, sidewalls 54, 55, 56 and 57 extend beyond projections 59 to form a barrier to the loss of fluid by evaporation when fitted into the device of the outer-base element and over the sample distribution element. The lid sidewalls further function to protect precoated projections from the outside environment prior to use. The sidewalls may also hold a removable seal element that protects the projections.

The device may be used for the rapid separation of a sample into numerous aliquots and the treatment of any or all of the aliquots with the same or different reagents, substrates or other chemical additives.

The device is suitable for identifying microbes such as *E. coli* and *Klebsiella pneumoniae* in sample aliquots. Substrates useful for the identification or differentiation of microbes may be added to each aliquot by manual pipetting or by using the lid projections of the device. Interaction of an organism and the substrate may be for example, detected by a chemical or optically detectable change such as color of the aliquot. Other identifying and differentiating methods may use the removable lid to deliver substrates to each aliquot to produce distinct reactions in each aliquot.

The present invention may be embodied in other specific forms without departing from the spirit or essential attributes thereof.

The example is not limited to any specific embodiment of the invention, but is only exemplary.

EXAMPLE 1

Method and Apparatus for Producing Multiple Aliquots Pipette Filling Vs Direct Filling Two devices A and B of the present invention molded of Polysar 555 polystyrene were utilized to demonstrate the ability of the invention to produce essentially equal aliquots of a sample. The units were first analyzed by recording their optical density in a dry state using a spectrophotometer (Dynatech Model MR700, Dynatech Laboratories, McLean, Va.) to make readings at 560 nanometers.

A solution of phenol red dye was prepared by dissolving 0.047 gin in 100 ml of a 0.067M phosphate buffer at pH 7.5. A pipette was utilized to dispense 0.0060 ml of the dye solution onto the projections of lid A. Sample distribution element A was filled with the dye solution and then covered with lid A.

Sample distribution element B was directly filled with a 10:1 dilution of the dye and covered with lid B which had no solution on the projections.

Table 1 shows the measured mean and standard deviations from the mean measured for each device.

TABLE 1

| Device | Mean OD at 560 NM | Standard Deviation | Coefficient of Variation (%) |
|---|---|---|---|
| A | 1.357 | 0.053 | 3.9% |
| B | 1.171 | 0.015 | 1.3% |

The procedure of dispensing the dye by pipette yielded a slightly higher coefficient of variation than direct filling. This is, in part, due to the relative difficulty of pipetting such small volumes. The coefficient of variation of less than 2% for device B, and less than 4% for device A, are adequately reproducible for procedures in analytical microbiology. This example also demonstrates the use of the lid projections to receive a liquid reagent, have reagent dried for storage and then have said dried reagent be reproducibly delivered and rehydrated or dissolved in the equal volume aliquots produced by the invention. Time required to produce the sample aliquots using the device of the present invention was less than 30 seconds.

What is claimed is:

1. A method for identifying microbes comprising:

(a) providing multiple aliquot device comprising a sample distribution element comprising an upper surface and a lower surface substantially parallel to each other, means for containing and/or guiding said sample associated with said upper surface, and at least one well disposed between said upper and lower surfaces wherein said well comprises an upper mouth opening that forms a substantially sharp junction with said upper surface, a lower mouth opening in said lower surface, a sidewall connecting said upper mouth opening with said lower mouth opening, and a sidewall bottom surface associated with said lower mouth opening; and an outer-base element associated with a portion of said sample distribution element comprising a bottom with an inner surface and at least one well bottom raised from said inner surface; wherein said sidewall bottom of said well of said sample distribution element and said well bottom of said outer-base element are substantially parallel to each other and from a spaced means to allow the escape of air;

(b) distributing liquid sample without air entrapment to said multiple aliquot device;

(c) subjecting said sample to at least one substrate useful for identifying and detecting microbes; and (d) examining said sample for chemical and optically detectable change so as to identify microbes in said sample.

2. A method of identifying microbes in a liquid sample comprising:

(a) providing a multiple aliquot device comprising a sample distribution element comprising an upper surface and a lower surface substantially parallel to each other, means for containing and/or guiding said sample associated with said upper surface, and at least one well disposed between said upper and lower surfaces wherein said well comprises an upper mouth opening that forms a substantially sharp junction with said upper surface, a lower mouth opening in said lower surface, a sidewall connecting said upper mouth opening with said lower mouth opening, and a sidewall bottom surface associated with said lower mouth opening; and an outer-base element associated with a portion of said sample distribution element comprising a bottom with an inner surface and at least one well bottom raised from said inner surface; wherein said sidewall bottom of said well of said sample distribution element and said well bottom of said outer-base element are substantially parallel to each other and form a spaced means to allow the escape of air and a lid removably covering said outer-base element and said sample distribution element comprising an upper surface, a lower surface, sidewalls adjacent to said upper surface and substantially perpendicular to said lower surface, and at least one projection depending from said lower surface which comprise reagents coated thereon;

(b) distributing said liquid sample without air entrapment into said multiple aliquot device;

(c) subjecting said sample to at least one reagent for microbe identification wherein said lid is inserted over and into said sample distribution element and said projection of said lid corresponds in location with and fits within said upper mouth opening of said well of said sample distribution element so that said reagent coated on said projection is subjected to said sample;

(d) examining said sample for chemical or optically detectable change; and (e) performing analysis on said sample to identify microbes.

* * * * *